United States Patent
Stefanchik et al.

(10) Patent No.: US 7,976,458 B2
(45) Date of Patent: Jul. 12, 2011

(54) INDEPENDENT ARTICULATING ACCESSORY CHANNEL

(75) Inventors: David Stefanchik, Morrow, OH (US); James T. Spivey, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 761 days.

(21) Appl. No.: 11/566,954

(22) Filed: Dec. 5, 2006

(65) Prior Publication Data

US 2008/0132758 A1   Jun. 5, 2008

(51) Int. Cl.
*A61B 1/00* (2006.01)
(52) U.S. Cl. .................. 600/104; 600/106; 600/114
(58) Field of Classification Search .................. 600/104, 600/106, 114, 153, 121–125
See application file for complete search history.

(56) References Cited

U.S. PATENT DOCUMENTS

| | | |
|---|---|---|
| 3,924,608 A | 12/1975 | Mitsui |
| 4,454,887 A | 6/1984 | Kruger |
| 4,520,817 A | 6/1985 | Green |
| 4,646,722 A | 3/1987 | Silverstein et al. |
| 4,697,576 A | 10/1987 | Krauter |
| 5,025,778 A | 6/1991 | Silverstein et al. |
| 5,040,715 A | 8/1991 | Green |
| 5,201,908 A | 4/1993 | Jones |
| 5,211,649 A | 5/1993 | Kohler et al. |
| 5,217,001 A | 6/1993 | Nakao et al. |
| 5,259,366 A | 11/1993 | Reydel et al. |
| 5,353,783 A | 10/1994 | Nakao et al. |
| 5,383,880 A | 1/1995 | Hooven |
| 5,386,817 A | 2/1995 | Jones |
| 5,400,770 A | 3/1995 | Nakao et al. |
| 5,431,322 A | 7/1995 | Green et al. |
| 5,433,721 A | 7/1995 | Hooven et al. |
| 5,460,168 A | 10/1995 | Masubuchi et al. |
| 5,482,197 A | 1/1996 | Green et al. |

(Continued)

FOREIGN PATENT DOCUMENTS

DE   10139153 A1   2/2003

(Continued)

OTHER PUBLICATIONS

A machine translation to English for Herrmann (EP1284120) is being provided.*

(Continued)

*Primary Examiner* — Thomas J Sweet
*Assistant Examiner* — Ryan Henderson

(57) ABSTRACT

Devices and methods useful for delivering tools and/or materials to a surgical site are disclosed. In one embodiment, an accessory device for an endoscope is provided and can include an elongate sheath and an accessory channel. The elongate sheath can be adapted to receive an endoscope therein, and it can include a mating element extending longitudinally between proximal and distal ends thereof. The accessory channel can be adapted to receive a tool therethrough and it can also have a mating element extending between proximal and distal ends thereof and adapted to slidably mate to the mating element formed on the elongate sheath. In certain exemplary embodiments, a distal portion of the accessory channel can be adapted to derail from at least a distal portion of the elongate sheath while a proximal portion of the accessory channel remains mated to a proximal portion of the elongate sheath. In use, the elongate sheath and the accessory channel can each provide a pathway for delivering tools and/or materials to a surgical site. The distal ends of elongate sheath and the accessory channel can be detached and positioned independently of one another to afford improved positioning or placement of the tools and/or materials received therethrough.

6 Claims, 8 Drawing Sheets

U.S. PATENT DOCUMENTS

| | | | |
|---|---|---|---|
| 5,489,256 | A | 2/1996 | Adair |
| 5,503,616 | A | 4/1996 | Jones |
| 5,518,163 | A | 5/1996 | Hooven |
| 5,518,164 | A | 5/1996 | Hooven |
| 5,630,782 | A | 5/1997 | Adair |
| 5,643,175 | A | 7/1997 | Adair |
| 5,651,491 | A | 7/1997 | Heaton et al. |
| 5,667,517 | A | 9/1997 | Hooven |
| 5,715,988 | A | 2/1998 | Palmer |
| 5,749,889 | A | 5/1998 | Bacich et al. |
| 5,762,256 | A | 6/1998 | Mastri et al. |
| 5,779,130 | A | 7/1998 | Alesi et al. |
| 5,782,396 | A | 7/1998 | Mastri et al. |
| 5,865,361 | A | 2/1999 | Milliman et al. |
| 5,944,654 | A | 8/1999 | Crawford |
| 5,954,259 | A | 9/1999 | Viola et al. |
| 6,032,849 | A | 3/2000 | Mastri et al. |
| 6,071,233 | A | 6/2000 | Ishikawa et al. |
| 6,109,500 | A | 8/2000 | Alli et al. |
| 6,179,776 | B1 | 1/2001 | Adams et al. |
| 6,264,087 | B1 | 7/2001 | Whitman |
| 6,315,184 | B1 | 11/2001 | Whitman |
| 6,352,503 | B1 | 3/2002 | Matsui et al. |
| 6,443,973 | B1 | 9/2002 | Whitman |
| 6,458,076 | B1 | 10/2002 | Pruitt |
| 6,522,101 | B2 | 2/2003 | Malackowski |
| 6,527,753 | B2 | 3/2003 | Sekine et al. |
| 6,569,085 | B2 | 5/2003 | Kortenbach et al. |
| 6,699,180 | B2 | 3/2004 | Kobayashi |
| 6,716,233 | B1 | 4/2004 | Whitman |
| 6,740,030 | B2 | 5/2004 | Martone et al. |
| 6,761,685 | B2 | 7/2004 | Adams et al. |
| 6,786,864 | B2 | 9/2004 | Matsuura et al. |
| 6,790,173 | B2 | 9/2004 | Saadat et al. |
| 6,793,652 | B1 | 9/2004 | Whitman et al. |
| 6,808,491 | B2 | 10/2004 | Kortenbach et al. |
| 6,824,509 | B2 | 11/2004 | Yamaya et al. |
| 6,846,307 | B2 | 1/2005 | Whitman et al. |
| 6,846,308 | B2 | 1/2005 | Whitman et al. |
| 6,846,309 | B2 | 1/2005 | Whitman et al. |
| 6,878,106 | B1 | 4/2005 | Herrmann et al. |
| 6,984,203 | B2 | 1/2006 | Tartaglia et al. |
| 6,997,931 | B2 | 2/2006 | Sauer et al. |
| 7,029,435 | B2 | 4/2006 | Nakao |
| 7,056,284 | B2 | 6/2006 | Martone et al. |
| 7,070,559 | B2 | 7/2006 | Adams et al. |
| 7,087,010 | B2 | 8/2006 | Ootawara et al. |
| 2002/0049454 | A1 | 4/2002 | Whitman et al. |
| 2002/0107530 | A1 | 8/2002 | Sauer et al. |
| 2002/0183591 | A1 | 12/2002 | Matsuura et al. |
| 2003/0036679 | A1 | 2/2003 | Kortenbach et al. |
| 2003/0130561 | A1 | 7/2003 | Suzuki et al. |
| 2003/0130564 | A1 | 7/2003 | Martone et al. |
| 2003/0176880 | A1 | 9/2003 | Long et al. |
| 2003/0195387 | A1 | 10/2003 | Kortenbach et al. |
| 2003/0208219 | A1 | 11/2003 | Aznoian et al. |
| 2004/0133075 | A1 | 7/2004 | Motoki et al. |
| 2004/0215058 | A1 | 10/2004 | Zirps et al. |
| 2004/0230095 | A1 | 11/2004 | Stefanchik et al. |
| 2004/0230096 | A1 | 11/2004 | Stefanchik et al. |
| 2004/0230097 | A1 | 11/2004 | Stefanchik et al. |
| 2005/0049455 | A1 | 3/2005 | Ootawara et al. |
| 2005/0119525 | A1 | 6/2005 | Takemoto |
| 2005/0124855 | A1 | 6/2005 | Jaffe et al. |
| 2005/0137454 | A1 | 6/2005 | Saadat et al. |
| 2005/0137455 | A1 | 6/2005 | Ewers et al. |
| 2005/0149067 | A1 | 7/2005 | Takemoto et al. |
| 2005/0154258 | A1 | 7/2005 | Tartaglia et al. |
| 2005/0165419 | A1 | 7/2005 | Sauer et al. |
| 2005/0177181 | A1 | 8/2005 | Kagan et al. |
| 2005/0222495 | A1 | 10/2005 | Okada et al. |
| 2005/0234297 | A1 | 10/2005 | Devierre et al. |
| 2005/0256374 | A1 | 11/2005 | Long et al. |
| 2006/0015009 | A1 | 1/2006 | Jaffe et al. |
| 2006/0020247 | A1 | 1/2006 | Kagan et al. |
| 2006/0079735 | A1 | 4/2006 | Martone et al. |
| 2006/0235271 | A1 | 10/2006 | Carter et al. |
| 2006/0258903 | A1 | 11/2006 | Stefanchik et al. |
| 2006/0258904 | A1 | 11/2006 | Stefanchik et al. |
| 2006/0259010 | A1 | 11/2006 | Stefanchik et al. |
| 2007/0225562 | A1 | 9/2007 | Spivey et al. |

FOREIGN PATENT DOCUMENTS

| | | |
|---|---|---|
| EP | 1 847 78 | 6/1986 |
| EP | 0 552 050 | 7/1993 |
| EP | 0 552 423 | 7/1993 |
| EP | 0 634 144 | 1/1995 |
| EP | 0 705 570 | 4/1996 |
| EP | 0 880 338 | 12/1998 |
| EP | 1 152 685 | 8/2000 |
| EP | 1 161 174 | 9/2000 |
| EP | 1 284 120 | 2/2003 |
| EP | 1 400 214 | 3/2004 |
| EP | 1 402 837 | 3/2004 |
| EP | 1 426 012 | 6/2004 |
| EP | 1 459 695 | 9/2004 |
| EP | 1477104 | 11/2004 |
| EP | 1 535 565 | 6/2005 |
| EP | 1 593 337 | 11/2005 |
| EP | 1 607 050 | 12/2005 |
| GB | 2109241 | 6/1983 |
| GB | 2272159 | 5/1994 |
| JP | 2000033071 | 2/2000 |
| JP | 2000171730 | 6/2000 |
| JP | 2000325303 | 11/2000 |
| JP | 2002143078 | 5/2002 |
| JP | 2005131107 | 5/2005 |
| JP | 2005131163 | 5/2005 |
| JP | 2005131164 | 5/2005 |
| JP | 2005131173 | 5/2005 |
| JP | 2005131211 | 5/2005 |
| JP | 2005131212 | 5/2005 |
| JP | 2005137423 | 6/2005 |
| JP | 2005152416 | 6/2005 |
| JP | 2005304586 A | 11/2005 |
| WO | WO-91/14391 | 10/1991 |
| WO | WO-97/29680 | 8/1997 |
| WO | WO-00/48506 | 8/2000 |
| WO | WO-00/54653 | 9/2000 |
| WO | WO-00/72762 | 12/2000 |
| WO | WO-00/72765 | 12/2000 |
| WO | WO-01/49165 | 7/2001 |
| WO | WO-01/56457 | 8/2001 |
| WO | WO-01/89624 | 11/2001 |
| WO | WO-02/43571 | 6/2002 |
| WO | WO-03/000138 | 1/2003 |
| WO | WO-03/015604 | 2/2003 |
| WO | WO-03/077769 | 9/2003 |
| WO | WO-2004/021868 | 3/2004 |
| WO | WO-2004/034875 | 4/2004 |
| WO | WO-2004/047626 | 6/2004 |
| WO | WO-2004/052426 | 6/2004 |
| WO | WO-2004/096015 | 11/2004 |
| WO | WO-2004/103157 | 12/2004 |
| WO | WO-2004/105593 | 12/2004 |
| WO | WO 2004105593 A1 * | 12/2004 |
| WO | WO-2005/016181 | 2/2005 |

OTHER PUBLICATIONS

U.S. Appl. No. 11/277,323, filed Mar. 23, 2006, Ortiz et al.
U.S. Appl. No. 11/277,324, filed Mar. 23, 2006, Ortiz et al.
Paul Breedveld, et al., "A New, Easily Miniaturized Sterrable Endoscope," IEEE Engineering in Medicine and Biology Magazine (Nov./Dec. 2005).
Frederick Van Meer, et al., "A Disposable Plastic Compact Wrist for Smart Minimally Invasive Surgical Tools," LAAS/CNRS, this paper appears in : Intelligent Robots and Systems, 2005. (IROS 2005). 2005 IEEE/RSJ International Conference on Aug. 2-6, 2005.
U.S. Appl. No. 11/627,542, filed Jan. 26, 2007, Vakharia et al.
U.S. Appl. No. 11/277,324, filed Mar. 23, 2006, Spivey et al.
International Search Report issued in International Application No. PCT/US2007/086370, International Searching Authority, May 6, 2008.

* cited by examiner

INDEPENDENT ARTICULATING ACCESSORY CHANNEL

FIELD OF THE INVENTION

The present invention generally relates to methods and devices for delivering tools and/or materials to a surgical site.

BACKGROUND OF THE INVENTION

Endoscopic surgical devices are often preferred over traditional open surgical devices because the use of a natural orifice tends to reduce post-operative recovery time and complications. Consequently, significant development has gone into a range of endoscopic surgical devices that are suitable for precise placement of a working end of a tool at a desired surgical site through a natural orifice. These tools can be used to engage and/or treat tissue in a number of ways to achieve a diagnostic or therapeutic effect.

The ability to manipulate a tool at a surgical site can be limited by the method or device with which it is placed at the site. For example, the devices and methods used to place a tool may restrict its movement relative to the surgical site and/or to other tools. At the same time, many endoscopic procedures require that surgical tools be positioned or used independently at the surgical site. For example, oftentimes an endoscope must be able to provide a view of a surgical site and/or the distal end of a surgical tool. In such cases it can be helpful if the endoscope has an unobstructed view of the surgical tool and is not blocked by the surgical tool itself. A procedure may also call for the cooperative use of two or more surgical tools and may necessitate precise placement and/or orientation of such tools with respect to one another. For example, one tool may be employed to manipulate or grasp tissue while another tool dissects the tissue.

Accordingly, there is a need for improved methods and devices for delivering tools and/or materials to a surgical site.

SUMMARY OF THE INVENTION

In one embodiment, a surgical device is provided having an elongate sheath and an accessory channel. The elongate sheath can be adapted to receive an endoscope therein and can have a mating element extending longitudinally between proximal and distal ends thereof. The accessory channel can be adapted to receive a tool therethrough and can have a mating element extending between proximal and distal ends thereof and adapted to slidably mate to the mating element formed on the elongate sheath. In certain exemplary embodiments, a distal portion of the accessory channel can be adapted to derail from at least a distal portion of the elongate sheath while a proximal portion of the accessory channel remains mated to a proximal portion of the elongate sheath.

The mating elements on the elongate sheath and the accessory channel can have a variety of configurations. In one embodiment, the mating element of at least one of the elongate sheath and the accessory channel can have a gap formed therein that is adapted to allow at least the distal portion of the accessory channel to derail from at least the distal portion of the elongate sheath. In one exemplary embodiment, the mating element of the elongate sheath can include a T-shaped track and the mating element of the accessory channel can include a T-shaped rail. At least one of the track and the rail can have a cutout formed therein that is adapted to allow at least the distal portion of the accessory channel to derail from at least the distal portion of the elongate sheath.

In another embodiment, the mating element of at least one of the elongate sheath and the accessory channel can include a track and an elongate retaining member. The elongate retaining member can be slidably mated to the track and adapted to move between a distal position in which a portion of the accessory channel proximal to a distal end of the retaining member is mated to a portion of the elongate sheath proximal to the distal end of the retaining member, and a proximal position in which a portion of the accessory channel distal to the distal end of the retaining member is derailed from a portion of the elongate sheath distal to the distal end of the retaining member. The retaining member and the track can have a variety of configurations. For example, in one exemplary embodiment the retaining member and the track can define a T-shaped channel when the retaining member is mated to the track. The retaining member can also include first and second elongate members adapted to slidably mate to opposed first and second sidewalls of the track.

Also provided is an endoscopic system, which in one embodiment can have an elongate sheath and an accessory channel. The elongate sheath can be adapted to receive an endoscope therein and it can have a track extending longitudinally between proximal and distal ends thereof. An endoscope can be disposed within the elongate sheath. The accessory channel can be adapted to receive a tool therethrough and can have a rail extending between proximal and distal ends thereof that is adapted to slidably couple to the track on the elongate sheath. In certain exemplary embodiments, at least one of the rail and the track can include a derailing feature formed thereon that is adapted to allow a distal portion of the accessory channel to derail from a distal portion of the elongate sheath. In some embodiments, the track and the rail can each be T-shaped.

The derailing feature of the system can have a variety of configurations, but in one embodiment the derailing feature can include a cutout formed therein and adapted to allow at least the distal portion of the accessory channel to derail from at least the distal portion of the elongate sheath. In another embodiment, the derailing feature can include a groove formed between proximal and distal ends of at least one of the rail and the track and an elongate retaining member slidably mated to the groove and adapted to move between a distal position in which a portion of the accessory channel adjacent to the retaining member is mated to a portion of the elongate sheath adjacent to the retaining member, and a proximal position in which a portion of the accessory channel distal to the retaining member is derailed from a portion of the elongate sheath distal to the retaining member. The elongate retaining member and the track can have a variety of configurations. For example, in one exemplary embodiment the elongate retaining member and the track can define a T-shaped channel when the retaining member is mated to the track. In another embodiment, the elongate retaining member can include first and second elongate members that are adapted to slidably mate to first and second grooves formed between proximal and distal ends of at least one of the rail and the track.

In other aspects, a surgical method is provided and in one embodiment includes slidably mating an accessory channel to an elongate sheath to position a distal end of the accessory channel in proximity to a distal end of the elongate sheath, and manipulating the accessory channel to detach the distal end of the accessory channel from the distal end of the elongate sheath while a proximal portion of the accessory channel remains mated to a proximal portion of the elongate sheath. In one embodiment, slidably mating the accessory channel to the elongate sheath can include advancing a rail extending along the accessory channel through a track extending along the elongate sheath. In another embodiment, manipulating the accessory channel can include proximally sliding an elongate retaining member coupled between the distal end of the elongate sheath and the distal end of the accessory channel. Manipulating the accessory channel can also include advancing a distal end of a mating element on the accessory channel through a gap formed in a mating element on the elongate sheath, and articulating the distal end of the accessory channel away from the distal end of the elongate sheath. In yet another embodiment, manipulating the accessory channel can include advancing the accessory channel to position the distal end of the elongate sheath in a gap formed in a mating element on the accessory channel, articulating the distal end of the accessory channel away from the distal end of the elongate sheath, and withdrawing the accessory channel such that a portion of the accessory channel distal to the gap is detached from the distal end of the elongate sheath.

The surgical methods disclosed herein can also have a variety of further features. In one exemplary embodiment, the method can include, prior to manipulating, inserting the accessory channel with the elongate sheath mated thereto through a body lumen. In another embodiment, the method can include steering the distal end of the accessory channel away from the distal end of the elongate sheath. In another embodiment, the method can include inserting a tool through a lumen in the accessory channel such that a distal end of the tool is spaced a distance apart from the distal end of the accessory channel. In yet another embodiment, the method can include inserting an endoscope into the elongate sheath.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are nonlimiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods useful for delivering tools and materials to a surgical site. In some cases access to the surgical site can be gained translumenally, i.e., through a body lumen and/or a natural orifice in the body. The devices and methods are also useful for delivering tools and materials to the working end of a viewing instrument such as an endoscope. Although some of the embodiments disclosed herein will be described in the context of an endoscopic procedure, the devices and methods are not limited to such applications. They may be used with a wide variety of viewing instruments and other tools. Moreover, they may be used in a wide range of other procedures including non-endoscopic procedures, such as laparoscopic and open procedures, and in virtually any medical procedure now or later in use.

Figure 1:
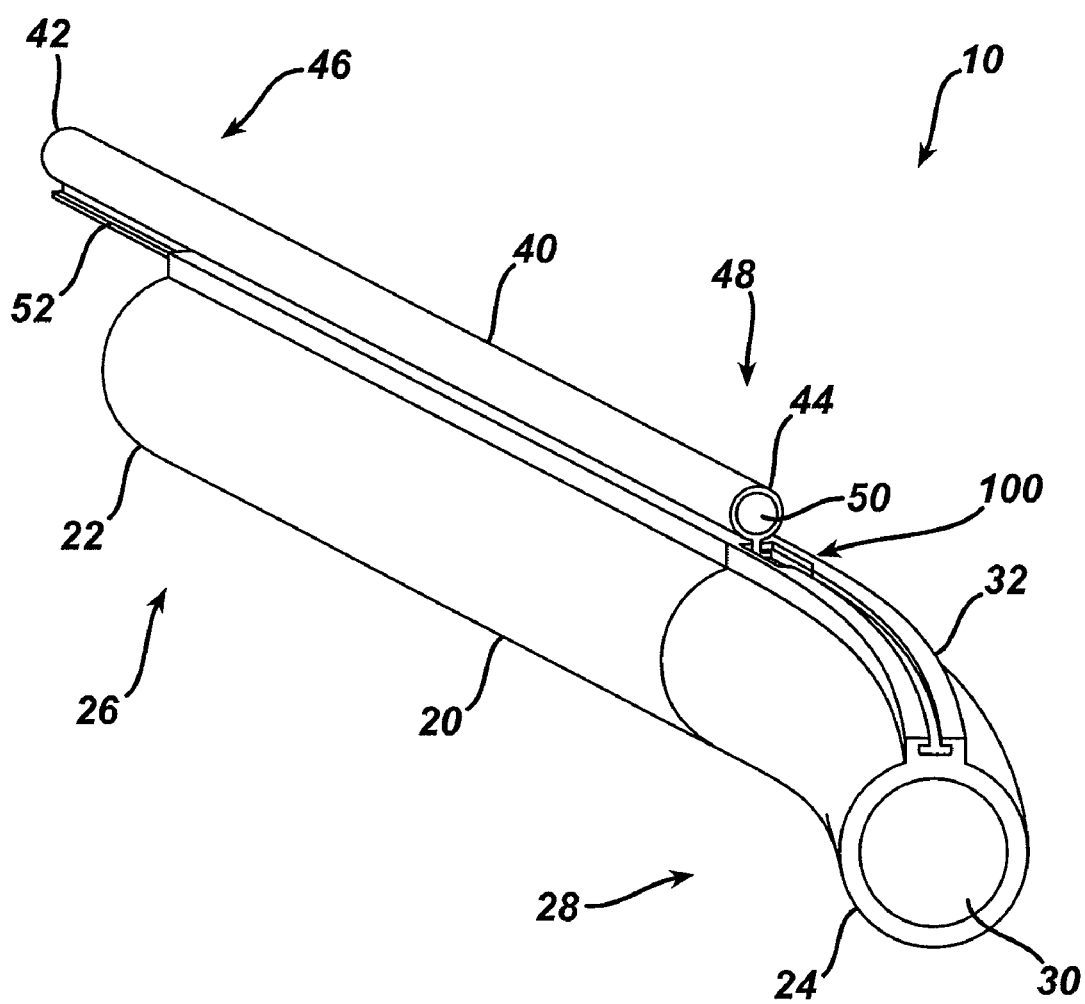
FIG. 1 is a perspective view of one exemplary embodiment of an accessory device having an elongate sheath with a track extending between proximal and distal ends thereof and an accessory channel with a rail extending between proximal and distal ends thereof.
Figure 2:
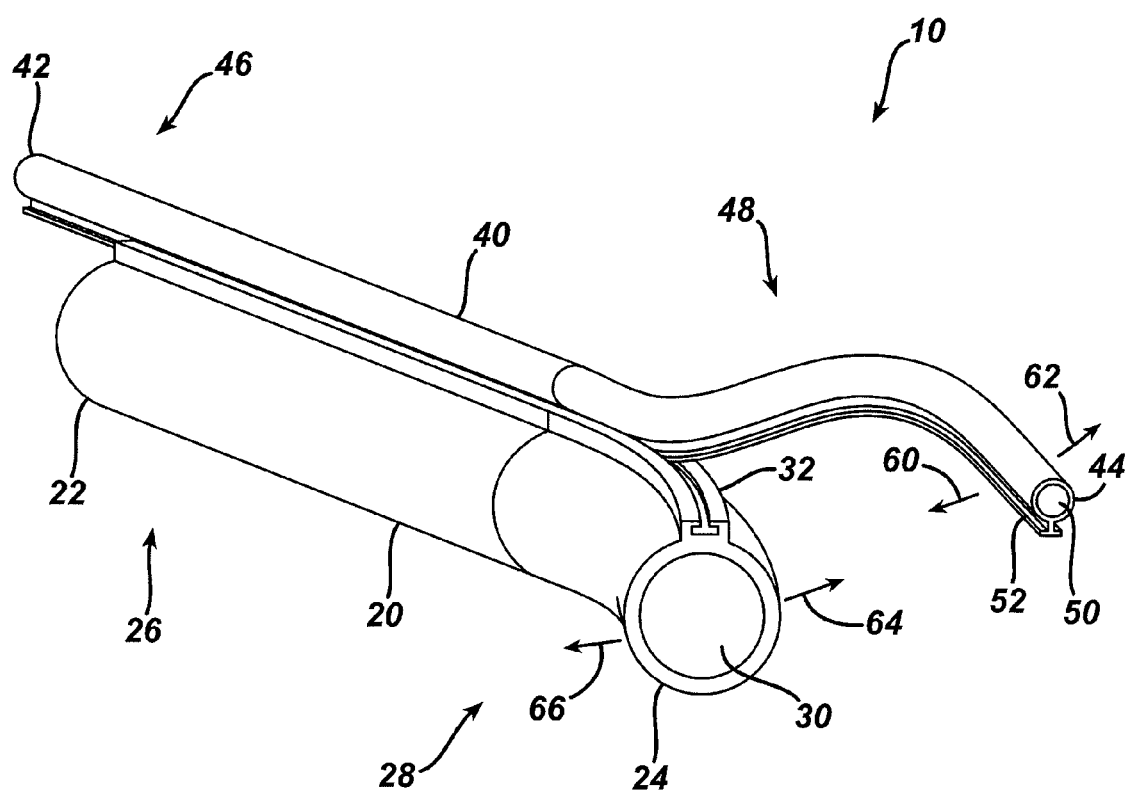
FIG. 2 is a perspective view of the device shown in FIG. 1 with a portion of the accessory channel derailed from a portion of the elongate sheath.

FIG. 1 illustrates one exemplary embodiment of accessory device 10. The accessory device 10 can have a variety of configurations, but in the illustrated embodiment the accessory device 10 has an elongate sheath 20 and an accessory channel 40. The elongate sheath 20 can have proximal and distal ends 22, 24 and a lumen 30 formed therethrough for receiving an endoscope, or other tool or material. The accessory channel can have proximal and distal ends 42, 44 and a lumen 50 formed therethrough for receiving a tool, such as a tissue-grasping device, or material, such as an irrigating fluid. As shown, the elongate sheath 20 and the accessory channel 40 can be mated or coupled to one another. In FIG. 1, the elongate sheath 20 and the accessory channel 40 each have a mating element which can serve to mate the elongate sheath 20 to the accessory device 40. The mating element on the accessory channel 40 is illustrated as a rail 52 that is T-shaped. The mating element on the elongate sheath 20 is illustrated as a track 32 for receiving a T-shaped rail 52 on the accessory channel 40 therein. By slidably mating the rail 52 to the track 32, as will be discussed in more detail below, the accessory channel 40 can be mated to the elongate sheath 20 and moved proximally and distally along the track 32. In an exemplary embodiment, the elongate sheath 20 and the accessory channel 40 can be adapted such that a distal portion 48 of the accessory channel 40 can be detached or derailed from a distal portion 28 of the elongate sheath 20. FIG. 2 shows the device of FIG. 1 with the distal end 44 of the accessory channel 40 derailed from the distal end 24 of the elongate sheath 20. Such a configuration can allow a tool disposed through the lumen 50 in the accessory channel 40 to be manipulated and/or positioned independently from an endoscope or other tool disposed in the lumen 30 in the elongate sheath 20. As further shown, a distal portion 40 of the accessory channel and/or a distal portion of the elongate sheath 20 can articulate or move relative to one another, as indicated by arrows 60, 62, 64, and 66.

The elongate sheath 20 can have a variety of configurations, but in an exemplary embodiment the elongate sheath 20 includes a proximal end 22 adapted to remain outside of the body and a distal end 24 adapted to be positioned within the body and adjacent to a surgical site. As such the elongate sheath 20 can have virtually any length. While the elongate sheath 20 can have a wide range of shapes, in the illustrated embodiment the elongate sheath 20 is a tube having a circular cross-sectional shape. Alternatively, the elongate sheath 20 can be a shaft, rod, sleeve, and so on, with a cross-sectional shape that is elliptical, oval, square, rectangular, or virtually any other shape, as one skilled in the art will recognize. The elongate sheath 20 can also have a lumen 30 formed therethrough that is adapted to receive a tool, device, or various materials therethrough. In an exemplary embodiment, the lumen 30 is configured to receive an endoscope therethrough such that the distal end of the endoscope is disposed at the distal end 24 of the elongate sheath 20 to view a surgical site. The elongate sheath 20 can, however, be adapted to fit any of a wide range of tools in a snugly-fitting or loosely-fitting manner, or can have a lumen 30 of a fixed or adjustable size or diameter irrespective of any tool. The lumen 30 can also serve as a passageway for surgical materials, such as irrigating fluids, antiseptic agents, organic material, and so on. Although in FIG. 1 the lumen 30 is depicted with an interior perimeter that is circular, which can be advantageous in receiving many kinds of tools and/or materials, the lumen 30 can have virtually any shape. Multiple lumens 30 also can be provided, in which case each lumen 30 can be used for a different tool or material. The elongate sheath 20 or portions thereof can also be flexible. For example, the elongate sheath 20 can be made of a flexible material or can include articulating segments placed in desired locations in order to provide a desired degree of suppleness. A flexible elongate sheath 20 can be advantageous in some applications, for example, to facilitate insertion through a tortuous body lumen or to create an elastic fit with a tool received in lumen 30. A flexible elongate sheath 20 can also accommodate articulation or steering of a tool residing in lumen 30, such as an endoscope with an articulating distal end. In other embodiments, the elongate sheath 20 can be integrally formed with an endoscope, or the mating element on the elongate sheath can be directly formed on the endoscope thus eliminating the need for an elongate sheath.

The accessory channel 40 can also have a wide variety of configurations. In FIG. 1, the accessory channel 40 is shown as an elongate tube having a proximal end 42 and a distal end 44. The tube can have virtually any length, including a same or a similar length as the elongate sheath 20. The accessory channel 40 can have virtually any cross-sectional shape, including those shapes mentioned previously with respect to the elongate shaft 20. In the illustrated embodiment, the accessory channel 40 has a circular cross-sectional shape that is smaller in diameter than that of the elongate sheath 20. The accessory channel 40, however, need not have any particular size relative to the elongate sheath 20 and can have a size, including a diameter, width, or other dimension, equal to, greater than or less than that of the elongate sheath 20. In some cases, the elongate sheath 20 can receive an endoscope therethrough and the accessory channel 40 can be smaller in diameter than the endoscope and/or the elongate sheath 20. The accessory channel 40 can also have a lumen 50 formed therein for receiving a tool or material therethrough. Multiple lumens 50 are possible, such as was described previously with respect to the elongate sheath 20. In other embodiments, the lumen 50 can be omitted and the accessory channel 40 can have a rigid portion and can be solid and/or can include a solid cap or distal tip, which can be advantageous in some applications for manipulating tissue, as will be discussed in more detail below. The accessory channel 40 or portions thereof can also be flexible or configured with articulating segments, which can be advantageous if the elongate sheath 20 is also flexible. For example, flexible portions of the accessory channel 40 can correspond to flexible portions of the elongate sheath 20 and can allow the device 10 to be flexible even when the accessory channel 40 is mated to the elongate sheath 20. A distal portion 48 or the distal end 44 of the accessory channel can also be adapted to be controllably articulated, as described in commonly owned U.S. patent application Ser. No. 11/277,324, entitled "Articulating Endoscopic Accessory Channel," of James T. Spivey et al., which is hereby incorporated by reference in its entirety. An example of articulation of the accessory channel 40 is illustrated in FIG. 2.

Figure 3A:
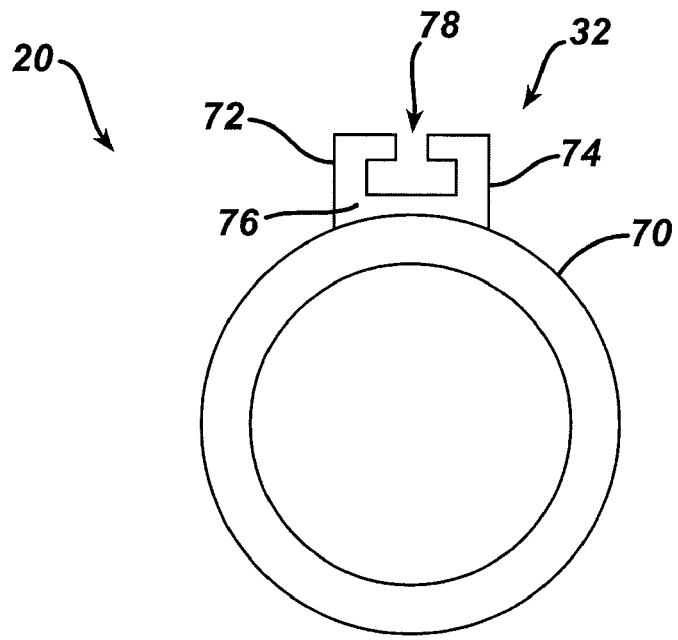
FIG. 3A is an end view of the distal end of the elongate sheath of the device shown in FIG. 1.
Figure 3B:
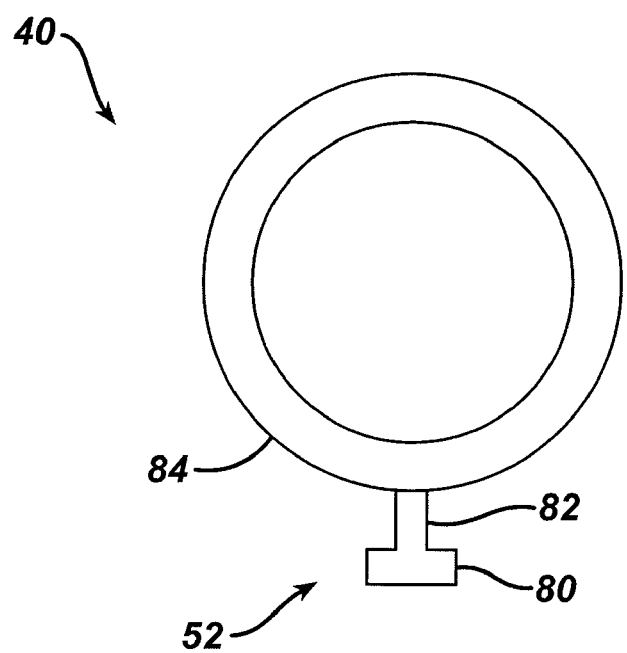
FIG. 3B is an end view of the distal end of the accessory channel of the device shown in FIG. 1.
Figure 3C:
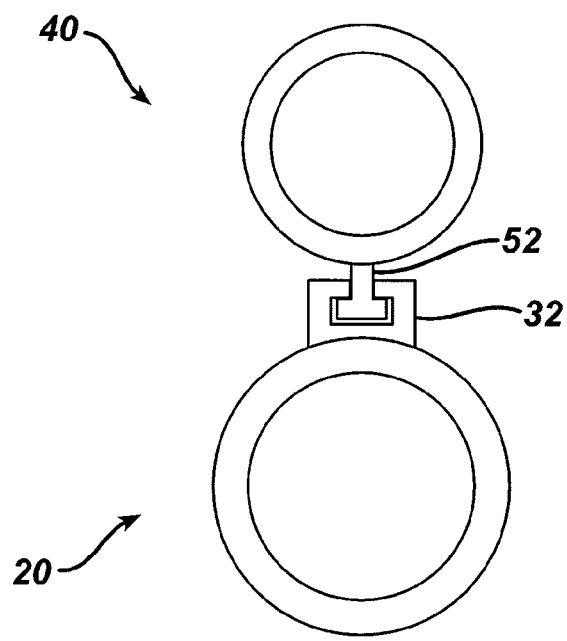
FIG. 3C is an end view of the distal end of the device shown in FIG. 1.
Figure 4:
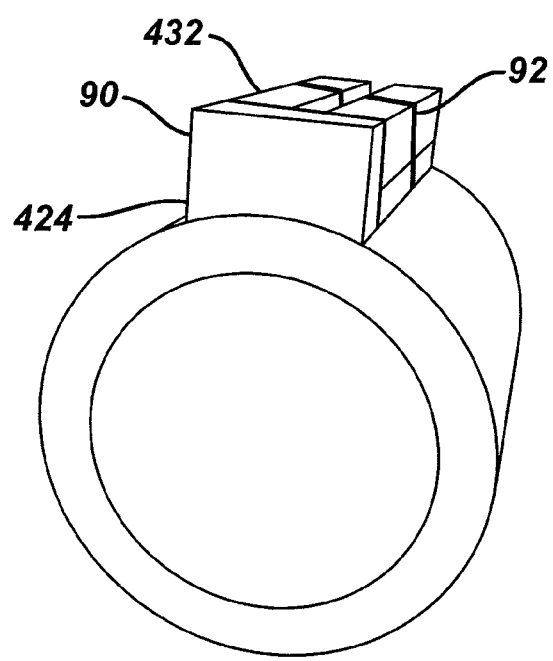
FIG. 4 is a perspective view of the distal end of the elongate sheath shown in FIG. 1 having an end cap disposed thereon.

As previously mentioned, the elongate sheath 20 and the accessory channel 40 can each have a mating element formed thereon and the mating elements can be adapted to mate with one another. The mating elements can have a variety of configurations, including for example interlocking elements, engaging elements, complementary shapes, sliding members, magnetic elements, spring-loaded retaining members, elastic members, and so on. Such elements can be formed on any portion of or along the entire length of the elongate sheath 20 and/or accessory channel 40. In an exemplary embodiment the mating element formed on the elongate sheath 20 is a track 26 disposed longitudinally along an outer surface 70 of the elongate sheath 20 between proximal and distal ends 22, 26 thereof, as shown in FIGS. 3A-3C. The track 32 can have virtually any length, although it can be advantageous if the track 32 is comparable in length to the elongate sheath 20 so that that accessory channel 40 can be securely mated thereto. The track 32 can have a first sidewall 72, an opposing second sidewall 74, and a bottom portion 76. In some cases the bottom portion 76 of the track 32 can be the exterior surface 70 of the elongate sheath 20. The first and second sidewalls 72, 74 and bottom portion 76 can define a T-shaped channel 78 therebetween. The channel 78 can be arranged to complement and accommodate the mating element of the accessory channel 40 or a portion thereof. The mating element of the accessory channel 40 is illustrated in FIG. 3B, and as shown the mating element of the accessory channel 40 is a T-shaped rail 52 having a lateral member 80 disposed atop a vertical member 82. The rail 52 can be disposed longitudinally on an exterior surface 84 of the accessory channel 40 between proximal and distal ends 42, 44 thereof. The rail 52 can have virtually any length, including a length differing from the length of the track 32 or other mating element of the elongate sheath 20. Moreover, as one skilled in the art will recognize, while for clarity the track 32 and the rail 52 are described and illustrated herein as coterminous with the elongate sheath 20 and the accessory channel 40, respectively, the proximal 22, 42 and distal ends 24, 44 of the track 32 and the rail 52 need not correspond to the proximal 22, 42 and distal ends 24, 44 of the elongate sheath 20 and/or accessory channel 40. FIG. 3C illustrates the track 32 mated to the rail 52. The track 32 and the rail 52 can be adapted to slide when mated, e.g., to allow the rail 52 to be advanced distally or withdrawn proximally along the track 32, as will be discussed in more detail below. In such a case, the interior surfaces of the track 32, i.e., in channel 78, can be smooth. However, it also possible that the track 32 have a notched, indented, or serrated surface to facilitate movement of the rail 52 between selectable positions. In another embodiment, the track 432 can also include an end cap 90 to prevent the distal end of the rail from advancing beyond the distal end 424 of the track 432, as shown in FIG. 4. In other embodiments, one or more of the track and rail, or other mating elements, can be rigid, semi-flexible, or flexible. A flexible track and/or rail can be advantageous in some applications, such as where the elongate shaft and/or accessory channel are flexible, or where it is desired that the track and the rail have an elastic fit, e.g., where the track elastically encases and/or releases the rail. The track and the rail can be adapted to be flexible using a variety of techniques. For example, they can be made of a flexible material, or they can include segments or joints therein, or a plurality of slits or cuts therein, such as the vertical slit 92 illustrated in FIG. 4.

Figure 5:
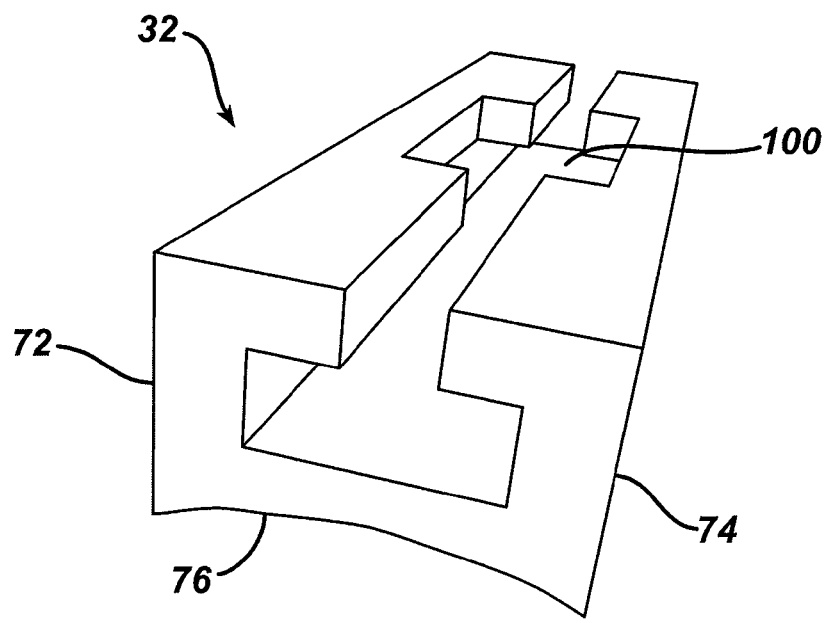
FIG. 5 is a perspective view of the track shown in FIG. 1 with a cut-out formed therein.
Figure 6:
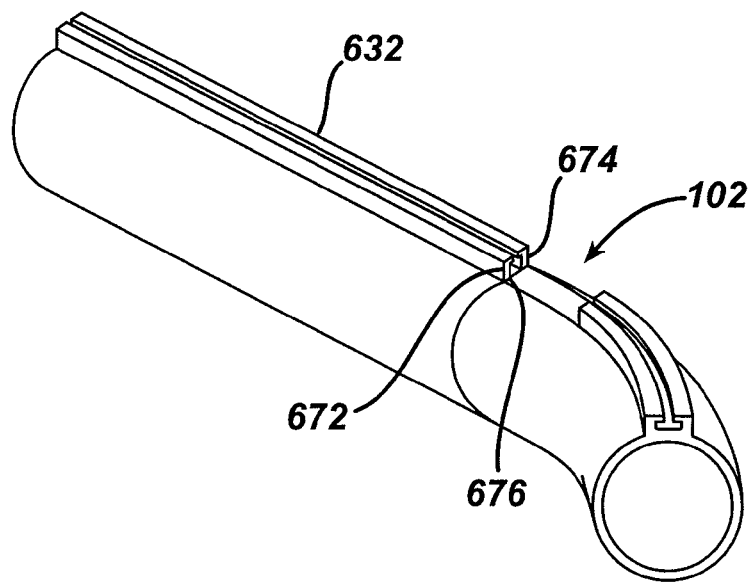
FIG. 6 is a perspective view of an alternate embodiment of an elongate sheath having a track with a gap formed therein.

As previously mentioned, the elongate sheath 20 and the accessory channel 40 can be adapted such that a distal portion 48 of the accessory channel 40 can be derailed from a distal portion 28 of the elongate sheath 20, preferably while the proximal portion 42 of the accessory channel 40 remains mated to the proximal portion 22 of the elongate sheath 20. These adaptations can take a wide variety of forms, and the derailed portion can have virtually any length. However, in an exemplary embodiment, as shown in more detail in FIG. 5, the track 32 of the elongate sheath 20 can include a gap 100 formed therein for allowing the accessory channel 40 to derail from the elongate sheath 20. The gap 100 can have a variety of configurations, and can be in the form of a space, opening, or cutout sufficient to allow the rail 52 to unmate from the track 32. The gap 100 can also have virtually any length, although it is preferable if the gap 100 is of sufficient length to allow the distal end 44 of the accessory channel 40 to derail from the elongate sheath 20 but not compromise the integrity of the mating between the elongate shaft 20 and accessory channel 40. As shown in FIG. 5, the gap 100 can be formed along a length of the top of the track 32. Alternatively, the gap can be such that the entire track is eliminated. For example, as shown in FIG. 6, a portion of the sidewalls 672, 674 and the bottom 676 of the track 632 can be omitted to form a gap 102. In other embodiments, a gap could be formed in one sidewall of the track but not another, allowing the accessory channel to derail only on the side of or in the direction of the gap. Multiple gaps of any length can also be included.

Figure 7:
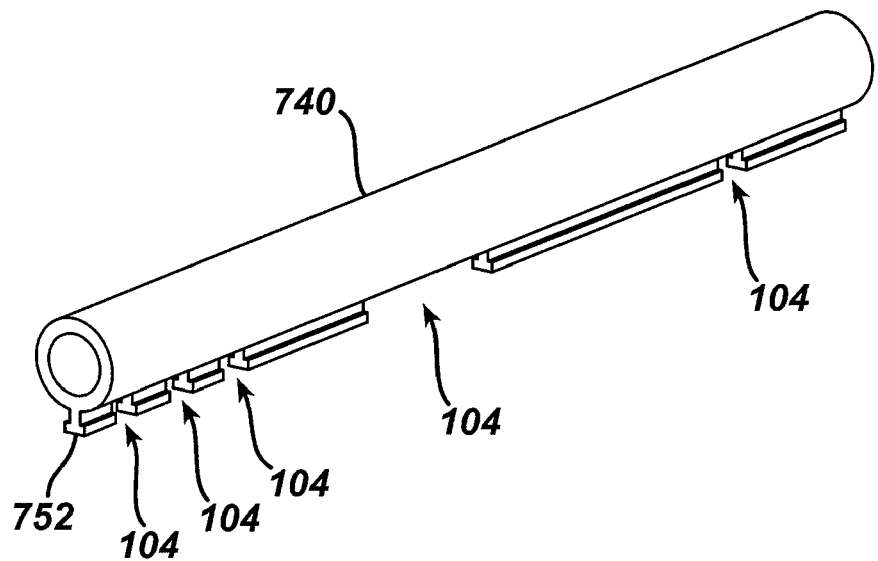
FIG. 7 is a perspective view of an alternate embodiment of an accessory channel having a rail with a plurality of gaps formed therein.

As one skilled in the art will appreciate, one or more gaps could alternatively or additionally be formed in the rail 52 or other mating element on the accessory channel 20. Such gaps can be configured in a wide variety of ways, and can have any length. In the embodiment shown in FIG. 7 a plurality of gaps 104 are formed in the rail 752 of the accessory channel 740, each gap 104 extending through the entire width of the rail 752. The gaps can also be formed only on a part of the rail 752 (e.g., a gap formed only in the lateral member), as previously described with respect to the gaps in the track.

Figure 8:
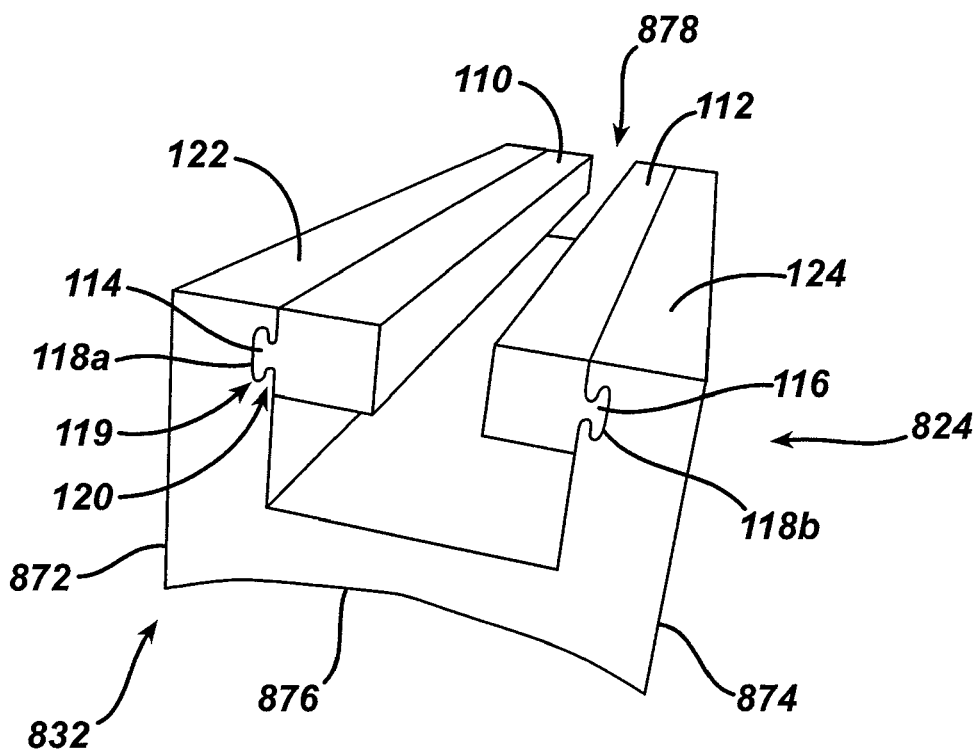
FIG. 8 is a perspective view of the distal end of an alternate embodiment of a track having a plurality of retaining members mated thereto.

In another embodiment shown in FIG. 8, the mating element, such as the track 832 of the elongate shaft and/or the rail of the accessory channel, can have one or more retaining members 110, 112 arranged such that a distal portion of the accessory channel can be derailed from a distal portion of the elongate sheath. The retaining members 110, 112 can have a variety of configurations, however in the illustrated embodiment, the retaining members 110, 112 are elongate members arranged as a longitudinal retaining edge or lip on the track. Rods, bar, cylinders, latches, pins, flaps, and a wide variety of other arrangements are also possible, including any arrangement that can retain the rail in the track 832. Moreover, while in FIG. 8 the retaining members 110, 112 have a substantially square cross-sectional shape, virtually any cross-sectional shape can be used, including elliptical, oval, rectangular etc. In use, the retaining members 110, 112 can be adapted to slide longitudinally along all or any portion of the track 832. Alternatively, the retaining members 110, 112 can be adapted to controllably recede or retreat into the bottom 876 or a sidewall 872, 874 of the track 832, for example via a spring-backed mechanism, to release the rail residing in the track 832, as will be discussed later in more detail. Each retaining member 110, 112 can also have a hinge element adapted to rotate or actuate such that each retaining member 110, 112 releases the rail, for example by rotating a retaining flap from a horizontal position to a vertical position against a sidewall 872, 874.

Figure 9:
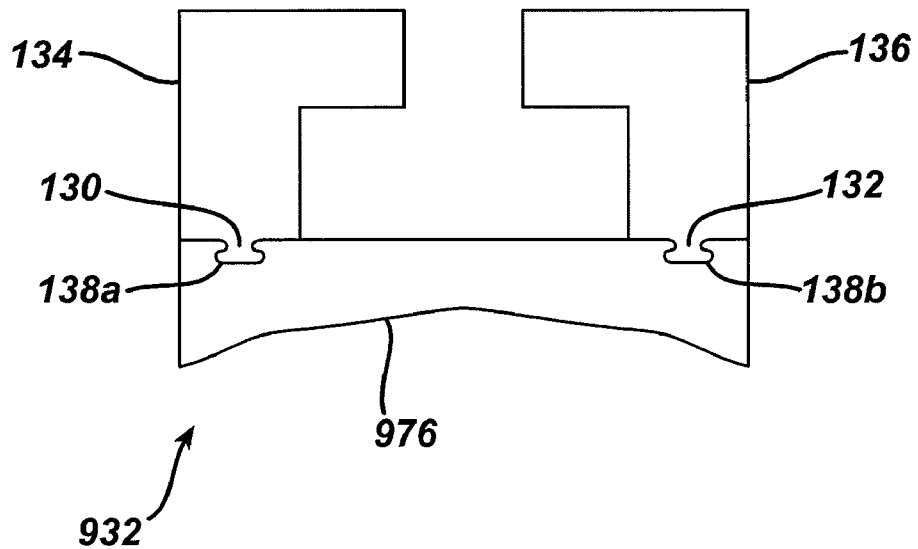
FIG. 9 is an end view of the distal end of an alternate embodiment of a track having a first and second retaining members mated thereto.

As further shown in FIG. 8, each retaining member 110, 112 can have a guide member 114, 116 adapted to couple to or mate with a groove 118a, 118b formed on the track 832. A wide variety of guide members 114, 116 and grooves 118a, 118b are possible, but as shown the guide members 114, 116 each have a narrow neck 119 and an expanded cap 120 or top in a mushroom-like shape. Other shapes, including T-shaped tapering, expanding, trapezoidal, dovetail, rectangular, keyed, non-keyed shapes, etc., can also be employed. The grooves 118a, 118b can have a shape complementary to that of the guide members 114, 116 and can be formed in a sidewall 872, 874 of the track 832. The guide members 114, 116 and the grooves 118a, 118b can be reversed, that is, one or more grooves 118a, 118b can be formed on one or more of the retaining members 110, 112, and the sidewalls 872, 874 of the track 832 can have the guide members 114, 116 protruding therefrom. In addition, while the grooves 118a, 118b are shown formed in the sidewalls 872, 874 of the track 832, respectively, the grooves 118a, 118b and the corresponding guide members 114, 116 can be disposed virtually anywhere on the track 832, including on the bottom 876 of the track, the tops 122, 124 of the sidewalls 872, 874, the exterior of the elongate sheath or the accessory channel, etc. For example, as shown in FIG. 9, the bottom 976 of the track 932 has two grooves 138a, 138b formed thereon, while two retaining members 134, 136, shown as L-shaped members, each have a guide member 130, 132 formed thereon.

Figure 10:
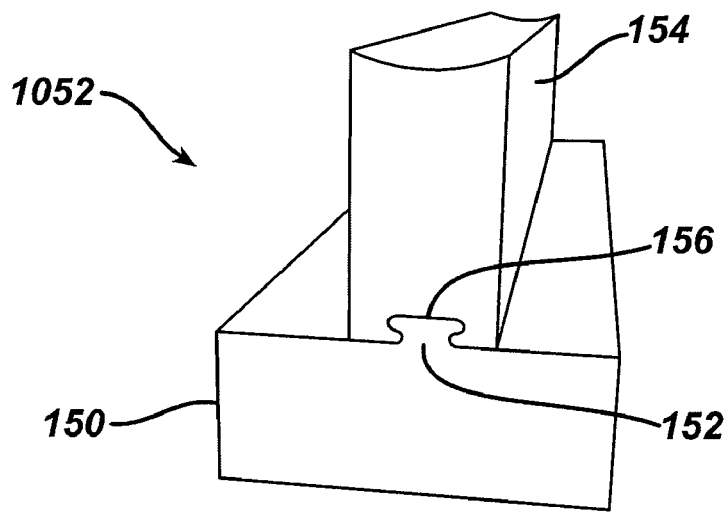
FIG. 10 is a perspective view of the distal end of an alternate embodiment of a rail having a retaining member mated thereto.
Figure 11:
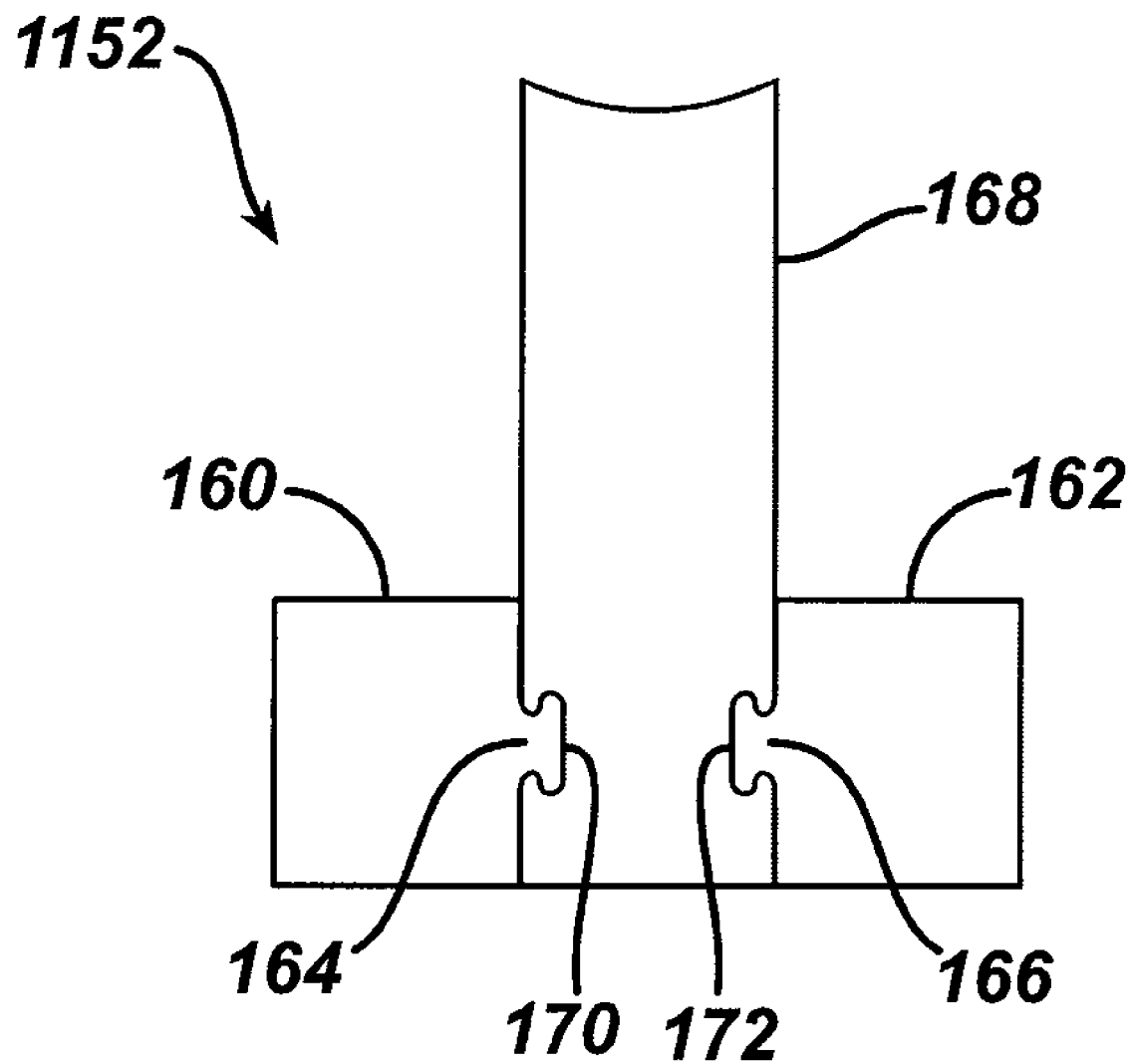
FIG. 11 is end view of a distal end of an alternate embodiment of a rail having first and second retaining members mated thereto.

In another embodiment, one more retaining members 150 can be formed on the rail 1052, as shown in FIG. 10. The retaining member 150 of the rail 1052 can have a wide variety of configurations including any of the configurations previously discussed with respect to the retaining members of the track. As shown, the retaining member 150 of the rail 1052 can have a guide member 152. While the location of the guide member can vary widely, in FIG. 10 the rail 1052 includes a retaining member 150 that is a lateral member disposed across a vertical wall 154 and has a guide member 152 extending into a groove 156 formed in the vertical wall 154. In another embodiment shown in FIG. 11, the rail 1152 includes two retaining members 160, 162, each having a guide member 164, 166 formed thereon. The rail 1152 of FIG. 11 also includes a vertical wall 168 with opposing grooves 170, 172 formed on opposing surfaces thereof.

As previously mentioned, in use the elongate sheath 20 and the accessory channel 40 can be configured such that a distal portion 48 of the accessory channel 40 can be detached or derailed from a distal portion 28 of the elongate sheath 20 while a proximal portion 46 of the accessory channel 40 preferably remains mated to a proximal portion 26 of the elongate sheath 20. In another embodiment, the end cap 90, shown in FIG. 4, can be omitted to leave the distal end 24 of the track 32 open. Alternatively, a portion of the end cap 90 can be retracted, folded, or otherwise moved such that the distal end 24 of the track 32 is open to free the rail 52 to move beyond the distal end 24 of the elongate sheath 20. In use, at least a distal portion 48 of the accessory channel 40 can be advanced beyond the distal end 24 of the elongate sheath 20, as will be discussed in more detail below.

As one skilled in the art will appreciate, the accessory device 10 of FIG. 1 can have a variety of other configurations. For example, it can include multiple elongate sheaths 20 and/or accessory channels 40. The elongate sheath 20, or a viewing instrument received therein, can be adapted to articulate in conjunction with or independently of the accessory channel 40. The mating elements as shown can be reversed, i.e., the elongate sheath 20 can have a rail 52 and the accessory channel 40 can have a track 32. Multiple mating elements can be provided, including additional tracks 32 and/or rails 52. A proximal handle can be provided and can have control elements, for example to control operation or movement of one or more retaining members 110, 112, to position of the accessory channel 20, to articulate the elongate sheath 20, or to operate a viewing instrument received in the elongate sheath 20 and/or the accessory channel 40. The integration of viewing instruments, irrigation devices, suction devices, illumination devices, and so on, into the device 10 are also possible.

The present invention also provides methods for positioning a surgical tool. In one exemplary method, an accessory device, such as the device 10 illustrated in FIG. 1, can receive a tool. Virtually any tool can be used, but in one exemplary embodiment the elongate sheath 20 can receive a viewing instrument such as an endoscope. The device 10 can be positioned in the body by inserting the distal end 24 of the elongate sheath 20 into a natural orifice such as the mouth, or through an incision made in the body. The device 10 can be advanced distally through a body lumen to a desired position. This insertion may be associated with or preceded by any number of procedures to lubricate, flex, shape, measure, steer, turn, rotate, and/or guide the elongate sheath 20 into the body. The insertion may also be assisted by or performed with a viewing instrument for showing the path of the device 10 within the body.

The accessory channel 40 can be mated to the elongate sheath 20 either prior to or after insertion of the elongate sheath 20 into the body. In the illustrated embodiment, the accessory channel 40 can be slidably mated to the elongate sheath 20 by sliding the distal end 44 of the rail 52 into the proximal end 22 of the track 32 and distally advancing the accessory channel 40. With the distal end of the accessory channel 40 and/or elongate sheath 20 positioned at a desired location within the body, at least a portion, e.g. a distal portion 48, of the accessory channel 40, can be derailed from at least a portion, e.g. a distal portion 28, of the elongate sheath 20. A proximal portion 48 of the accessory channel 40 can remain mated to a proximal portion 28 of the elongate sheath 20 during or after this derailing. Derailing can be performed using a wide variety of techniques, and can depend on the adaptations or derailing features provided on the mating elements of the elongate sheath 20 and/or accessory channel 40, as previously described. However, in one exemplary embodiment, the distal end 44 of the accessory channel 40 can be positioned in a gap formed in a mating element formed on the elongate sheath 20, such as the gap 100 in the track 32 shown in FIG. 5. The distal end 44 (or a distal portion 48) of the accessory channel 40 can be steered away from the elongate sheath 20, e.g., by operating a control to bend the distal end 44 of the accessory channel 40 laterally away from the elongate sheath 20. The accessory channel 40 can be distally advanced during or after being steered so as to extend the derailed portion and/or to position the distal end 44 of the accessory channel 40 independently from the elongate sheath 20. Alternatively, a distal portion 48 of the accessory channel 40 can be derailed by advancing the accessory channel 40 such that the distal end 24 of the elongate shaft 20 is disposed within a gap formed in a mating element on the accessory channel 40, such as one of the gaps 104 formed in the rail 752 shown in FIG. 7. The distal end 44 of the accessory channel 40, and/or optionally the distal end 24 of the elongate sheath 20, can be steered such that the distal end 44 of the accessory channel 40 is displaced from the distal end 24 of the elongate sheath 20. With the distal end 24 articulated, the accessory channel 40 can be withdrawn proximally such that a distal portion 48 of the accessory channel 40 remains derailed after the withdrawal.

In another exemplary derailing technique, one or more retaining members, such as one or more of the retaining members 110, 112, 134, 136, 150, 160, 162 illustrated in FIGS. 8-11, can be manipulated to derail or unmate at least a portion of the accessory channel 40 from at least a portion of the elongate sheath 20. For example, the retaining members 110, 112 in FIG. 8 can be withdrawn proximally to remove the retaining edge or lip of the track 832 and release the rail 52 of the accessory channel 40 disposed therein. Derailing can be controlled by the positioning of the retaining members 110, 112. For example, the part of the rail 52 distal to the distal end 824 of the retaining members 110, 112 can be derailed from the elongate sheath 20 and the part of the rail 52 proximal to the distal end 824 of the retaining members 110, 112 can remain mated the elongate sheath 20. The retaining members, 110, 112, if more than one, can be manipulated in a variety of ways. The retaining members 110, 112 can be manipulated together or independently, via a motorized mechanism or manually. The retaining members 110, 112 can also be manipulated by a control on a proximal handle or other device external to the body for controlling or aiding their movement.

In yet a further example of a derailing technique, the track 32 can have an open distal end 24 and the distal end 44 of the accessory channel 40 can be advanced distally beyond the distal end 24 of the elongate sheath 20 to derail the part of the accessory channel 40 distal to the distal end 24 of the elongate sheath 20. The distal end 44 of the accessory channel 40 can be advanced to virtually any position. For example, the accessory channel 40 can be advanced such that it becomes visible through a viewing instrument, such as an endoscope, disposed in the lumen 30 of the elongate sheath 20. In other embodiments, the accessory channel 40 can be used as a stiff arm, for example by advancing a rigid portion of the accessory channel 40 beyond the distal end 24 of the elongate sheath 20 to manipulate or hold tissue. The use of the accessory channel 40 as a stiff arm can be advantageous if the accessory channel 40 is solid and/or has a solid cap or distal tip, as previously described.

A distal portion 28 of the elongate sheath 20 and/or a distal portion 48 of the accessory shaft 40 can be positioned relative to one another and/or a surgical site. Virtually any type of positioning is possible and can be suited to the application at hand. Positioning can take a variety of forms and can include many stages or manipulations. For example, the elongate sheath 20 and/or the accessory channel 40 can be articulated, steered, flexed, slid proximally or distally, and so on.

Surgical tools and/or materials can be received through the elongate sheath 20 or the accessory channel 40, for example through their lumens 30, 50, and delivered to a surgical site. A wide array of surgical tools and materials can be used. For example, a grasping device can be employed in the lumen 50 of the accessory channel 40 while an endoscope received in the elongate sheath 20 provides a view of the distal end of the grasping device. Irrigating fluids can also be delivered through the accessory channel 40, endoscope, or elongate sheath 20 to a surgical site. Multiple tools can be delivered through the elongate sheath 20 (or the endoscope disposed therein) and/or the accessory channel 40. Tools and/or materials can also be withdrawn through the lumens 30, 50. For example, body tissue can be removed from the surgical site through the accessory channel 40 with the previously mentioned grasping device.

Once the procedure is complete, at least a portion of the accessory channel 40 can be remated to at least a portion of the elongate sheath 20. Such mating can be accomplished using a wide variety of techniques. In some cases, however, the technique employed can mirror one of the derailing techniques described previously. For example, the distal end 44 of the accessory channel 48 can be steered towards the track 32 on the elongate sheath 20 so as to be disposed in a gap formed therein, such as the gap 100 shown in FIG. 5. The accessory channel 40 can then be advanced proximally to slidably mate the accessory channel 40 to the elongate sheath 20. In another embodiment, if the accessory channel 40 was previously derailed by manipulating retaining members 110, 112, the accessory channel 40 can be mated by again manipulating the retaining members 110, 112. For example by distally advancing the retaining members 110, 112 to re-establish a retaining edge on the track 832. As the retaining members 110, 112 advance distally they can cause the rail of the accessory channel 40 to re-enter the channel 878 of the track 832.

Additional aspects of such a surgical procedure, which will be recognized by one skilled in the art, can include the repeated mating and/or unmating or derailing of the accessory channel 40 from the elongate sheath 20, the repeated removal and/or insertion of tools and materials through the lumens 30, 50, and additional positioning of the device 10, including steering or articulation of the accessory channel 40, the elongate sheath 20, and/or an endoscope that may be received through the elongate sheath 20. Yet further aspects can include removing and reintroducing the accessory channel 40, for example by sliding the accessory channel 40 proximally and distally on the elongate sheath 20, and the eventual withdrawal of the device 10 from the body.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning and/or replacement, and reassembly. Use of such techniques, and the resulting reconditioned device, are all within the scope of the present application.

Preferably, the invention described herein will be processed before surgery. First, a new or used tool is obtained and if necessary cleaned. The tool can then be sterilized. In one sterilization technique, the tool is placed in a closed and sealed container, such as a plastic or TYVEK bag. The container and tool are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that the device is sterilized. This can be done by any number of ways known to those skilled in the art including beta or gamma radiation, ethylene oxide, or steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An accessory device for an endoscope, comprising:
   an elongate sheath adapted to receive an endoscope therein; and,
   an accessory channel adapted to receive a tool therethrough, the elongate sheath and the accessory channel each having a mating element extending between respective proximal and distal ends thereof and adapted to slidably mate to one another and thereby couple the elongate sheath and the accessory channel, wherein one of the mating elements comprises a track and the other mating element comprises a rail;
   wherein at least one sidewall of one of the rail and the track is slidable to form an elongate retaining member adapted to move relative to each of the mating element of the accessory channel and the mating element of the elongate sheath, so as to derail at least a portion of the accessory channel distal to a distal end of the retaining member from a portion of the elongate sheath distal to the distal end of the retaining member.

2. The device of claim 1, wherein the mating element that has the elongate retaining member slidably mated thereto comprises the rail.

3. The device of claim 1, wherein the mating element that has the elongate retaining member slidably mated thereto comprises the track.

4. The device of claim 3, wherein the retaining member and the track define a T-shaped channel when the retaining member is mated to the track.

5. The device of claim 3, wherein the retaining member includes first and second elongate members adapted to slidably mate to opposed first and second sidewalls of the track.

6. A method for positioning a tool, comprising:
   slidably mating a mating element on an accessory channel with a mating element on an elongate sheath to position a distal end of the accessory channel in proximity to a distal end of the elongate sheath; and
   sliding an elongate retaining member formed on one of the mating elements in a proximal direction relative to each of the mating element on the accessory channel and the mating element on the elongate sheath to form an opening in one of the mating elements at a location proximal to a distal end of the accessory channel or the elongate shaft, thereby detaching a distal portion of the accessory channel from a distal portion of the elongate sheath while a proximal portion of the accessory channel remains mated to a proximal portion of the elongate sheath; wherein the mating element of the elongate sheath comprises a T-shaped track defining a T-shaped channel and the mating element of the accessory channel comprises a T-shaped rail slidably mating in the T-shaped channel.

* * * * *